(12) United States Patent
Piotrowski et al.

(10) Patent No.: US 10,208,187 B2
(45) Date of Patent: Feb. 19, 2019

(54) REACTIVE FLAME RETARDANTS FOR FLEXIBLE POLYURETHANE FOAMS

(71) Applicant: ICL-IP America Inc., Tarrytown, NY (US)

(72) Inventors: Andrew Piotrowski, Yorktown Heights, NY (US); Joseph Zilberman, Haifa (IL); Jeffrey Stowell, Wingdale, NY (US); Mark Gelmont, Haifa (IL); Mayank Singh, White Plains, NY (US); Zhihao Chen, Floral Park, NY (US); Eran Gluz, Hod Hasharon (IL)

(73) Assignee: ICL-IP America Inc., Tarrytown, NY (US)

(*) Notice: Subject to any disclaimer, the term of this patent is extended or adjusted under 35 U.S.C. 154(b) by 0 days.

(21) Appl. No.: 16/041,893

(22) Filed: Jul. 23, 2018

(65) Prior Publication Data
US 2019/0023873 A1   Jan. 24, 2019

Related U.S. Application Data

(60) Provisional application No. 62/536,260, filed on Jul. 24, 2017.

(51) Int. Cl.
| | | |
|---|---|---|
| *C08G 18/16* | (2006.01) | |
| *C08G 18/18* | (2006.01) | |
| *C08G 18/24* | (2006.01) | |
| *C08G 18/38* | (2006.01) | |
| *C08G 18/42* | (2006.01) | |
| *C08G 18/48* | (2006.01) | |
| *C08G 18/76* | (2006.01) | |
| *C08J 9/00* | (2006.01) | |
| *C08J 9/30* | (2006.01) | |
| *C08K 5/5313* | (2006.01) | |
| *G10K 11/162* | (2006.01) | |
| *C08G 101/00* | (2006.01) | |

(52) U.S. Cl.
CPC .......... *C08K 5/5313* (2013.01); *C08G 18/165* (2013.01); *C08G 18/18* (2013.01); *C08G 18/244* (2013.01); *C08G 18/42* (2013.01); *C08G 18/4829* (2013.01); *C08G 18/7614* (2013.01); *C08J 9/0038* (2013.01); *C08J 9/30* (2013.01); *C08G 18/388* (2013.01); *C08G 18/3878* (2013.01); *C08G 2101/00* (2013.01); *C08J 2201/022* (2013.01); *C08J 2375/06* (2013.01); *C08J 2375/08* (2013.01); *G10K 11/162* (2013.01)

(58) Field of Classification Search
CPC ............... C08K 5/5313; C08G 18/388; C08G 18/3878; C08J 9/0038
See application file for complete search history.

(56) References Cited

U.S. PATENT DOCUMENTS

| | | | |
|---|---|---|---|
| 2,372,244 A | | 3/1945 | Adams et al. |
| 3,249,562 A | | 5/1966 | Schoepfle et al. |
| 3,317,638 A | | 5/1967 | Hartman et al. |
| 3,597,509 A | | 8/1971 | Haus-Eberhard et al. |
| 3,639,532 A | | 2/1972 | Oertel et al. |
| 3,644,595 A | | 2/1972 | Wu |
| 4,407,981 A | * | 10/1983 | Aaronson .......... C08G 18/2885 521/107 |
| 6,090,968 A | | 7/2000 | Horold et al. |
| 2011/0201733 A1 | | 8/2011 | Hill et al. |
| 2011/0213062 A1 | | 9/2011 | Hill et al. |
| 2011/0224339 A1 | | 9/2011 | Hill et al. |
| 2011/0237722 A1 | | 9/2011 | Hill et al. |
| 2011/0245386 A1 | | 10/2011 | Hill et al. |
| 2011/0251312 A1 | | 10/2011 | Hill et al. |
| 2011/0281983 A1 | | 11/2011 | Hill et al. |
| 2012/0010312 A1 | | 1/2012 | Balbo Block et al. |
| 2016/0083500 A1 | | 3/2016 | Balbo Block et al. |
| 2016/0137676 A1 | * | 5/2016 | Rhudy .................. C09K 21/12 521/165 |

FOREIGN PATENT DOCUMENTS

| | | |
|---|---|---|
| GB | 1083939 A1 | 9/1967 |
| GB | 1215106 A1 | 12/1970 |
| GB | 2000535 A | 1/1979 |
| WO | 2010051884 A1 | 3/2010 |
| WO | 2014170316 A1 | 10/2014 |
| WO | 2017083463 A1 | 5/2017 |
| WO | 2017083468 A1 | 5/2017 |
| WO | 2017083471 A1 | 5/2017 |

OTHER PUBLICATIONS

Zhurnal Obshchei Khimi; Sep. 18, 1971.
U.S. Appl. No. 16/041,982, filed Jul. 23, 2018, claims provided.
PCT Patent Application No. PCT/US18/43228, filed Jul. 23, 2018, claims provided.
PCT Patent Application No. PCT/US18/43219, filed Jul. 23, 2018, claims provided.
PCT Patent Application No, PCT/US18/43218, filed Jul. 23, 2018, claims provided.
International Search Report and Written Opinion from PCT/US2018/043218 dated Oct. 18, 2018.
(Continued)

*Primary Examiner* — Melissa A Rioja
(74) *Attorney, Agent, or Firm* — Dilworth & Barrese, LLP

(57) ABSTRACT

The present invention provides dialkyl phosphorus-containing compounds, namely reactive mono-hydroxyl-functional dialkyl phosphinates, serving as highly efficient reactive flame retardants in flexible polyurethane foams. The invention further provides fire-retarded polyurethane compositions comprising said the reaction product of the mono-hydroxyl-functional dialkyl phosphinates with polyol and isocyanate foam forming components.

12 Claims, No Drawings

(56) References Cited

OTHER PUBLICATIONS

International Search Report and Written Opinion from PCT/US2018/043219 dated Oct. 19, 2018.
International Search Report and Written Opinion from PCT/US2018/043288 dated Oct. 19, 2018.

* cited by examiner

REACTIVE FLAME RETARDANTS FOR FLEXIBLE POLYURETHANE FOAMS

CROSS REFERENCE TO RELATED APPLICATION

This application claims the benefit of U.S. provisional patent application Ser. No. 62/536,260, filed Jul. 24, 2017, the entire contents of which are incorporated by reference herein.

FIELD OF THE INVENTION

The disclosure herein provides for the use of reactive dialkyl phosphorus-containing compounds, namely hydroxyl-functional esters of dialkyl phosphinic acids, which when reacted with polyol and isocyanate, serve as highly efficient reactive flame retardants in flexible polyurethane foams. The invention further provides fire-retarded flexible polyurethane foam with said hydroxyl-functional dialkyl phosphinates reacted and incorporated into the polymer matrix of a flexible polyurethane foam. The expressions "fire retardants" and "flame retardants" are used herein interchangeably.

BACKGROUND OF THE INVENTION

Brominated or phosphorus-based flame retardants are known to be highly effective and, in many cases, are the only options for reducing the fire risk of synthetic materials such as flexible polyurethane foams. However, the growing public and governmental scrutiny of chemicals, and in particular flame retardants, has increased over the years. The goal is towards more sustainable, reactive, polymeric and/or halogen-free new products. Scrutiny greatly diminishes if a flame retardant is reacted into the polymer matrix and cannot be leached-out.

Thus, there is a demand for reactive phosphorus-containing fire retardants for flexible polyurethane possessing such features as high phosphorus content, clear light color and good compatibility with polyether polyols and polyester polyols employed in the polyurethane industry.

SUMMARY OF THE INVENTION

The present invention provides reactive dialkyl phosphorus-containing mono-hydroxyl-functional compounds possessing highly satisfactory flame-retarding characteristics and having good compatibility with the polyol components of a flexible polyurethane foam-forming system. The expression "a flexible polyurethane foam-forming system" as used herein shall be understood to comprise a polyol, an isocyanate and a reactive dialkyl phosphorous-containing mono-hydroxyl functional compound as described herein. The mono-hydroxyl-functional dialkyl phosphinate compounds are fully reactive through their single hydroxyl-functional group, and can be more easily formulated than di- or tri-hydroxyl-functional dialkyl phosphinate compounds. It has been surprisingly found that despite its lower content of hydroxyl-functionality, the reactive mono-hydroxyl functional dialkyl phosphinate compounds herein can be reacted and incorporated into the polymer structure of a flexible polyurethane foam, e.g., by reaction with the isocyanate component of the flexible polyurethane foam-forming system, without disrupting the elastic properties of the flexible polyurethane foam. This means that the flame retardants of the invention become integrated into the flexible foam substrate, such that they are not released into the environment and are not likely to penetrate through cell membranes of living tissue, and therefore do not pose a health hazard. The invention further provides the flexible polyurethane foam-forming system described above, including but not limited to the reactive dialkyl phosphorus-containing mono-hydroxyl-functional compounds described herein.

The term "foam" as used herein refers to flexible polyurethane foams. The flexible polyurethane foam described herein, or claimed herein, as comprising, consisting essentially of, or consisting of the reacted mono-hydroxyl-functional dialkyl phosphinate compounds of the general formula (I-A) and/or (I-B), with the general formula (1-B) representing the group of phosphorus-containing diol and/or polyol reaction products of the partial phosphorylation of polyalcohols, which contain at least one phosphorus-containing group, are all understood herein to contain the aforementioned formula(e) as reactive materials, i.e., the aforementioned formula(e) are reacted into the flexible polyurethane material's structure, in which case the aforementioned formula(e) may not be present, or would not be present in the same structural formula(e) as described herein, but would be present in the flexible polyurethane material as a reaction product of a diol and/or polyol, an isocyanate and the structural formula(e) described herein.

The term "polyol" as used herein will be understood as also possibly being defined as a diol and/or a polyol.

The present invention provides mono-hydroxyl-functional dialkyl phosphinate compounds of the general formula (I-A) and (I-B), and a group of phosphorus-containing diol and/or polyol reaction products of the partial phosphorylation of polyalcohols, which contains at least one phosphorus-containing group of the general formula (I-B), wherein formula (I-A) is:

(I-A)

wherein:

$R^1$ and $R^2$, are selected from a linear or branched alkyl group containing from 1 to 4 carbon atoms, such as methyl, ethyl, propyl, isopropyl, butyl, and isobutyl, preferably methyl or ethyl, more preferably both $R^1$ and $R^2$ being ethyl; and, X is either ------$(Z)_k$—$R^3$ or

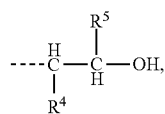

and when X is ------$(Z)_k$—$R^3$, Z is —$(Y—O)_n$—, wherein Y is a linear or branched alkylene group containing from 2 to 8 carbon atoms, preferably from 2 to 4 carbon atoms, more preferably ethylene, propylene, or isopropylene, and n represents an integer from 1 to 20, preferably from 1 to 5, and even more preferably from 1 to 2.

k may be 0 or 1;

$R^3$ is selected from hydrogen, a mono-hydroxy-terminated linear or branched alkylene group containing from 2 to about 8 carbon atoms, preferably from 2 to 4 carbon atoms; and, provided that when k is zero, $R^3$ is the mono-hydroxy-terminated linear or branched alkylene group and when k is 1, $R^3$ is hydrogen, and when X is

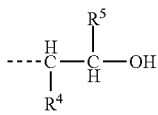

$R^4$ and $R^5$ are each independently selected from H, a linear or branched alkyl group containing from 1 to 8 carbon atoms, preferably from 1 to about 4 carbon atoms, and most preferably any one of methyl, ethyl or propyl, a linear or branched alkenyl group containing from 2 to 8 carbon atoms, preferably from 2 to about 4 carbon atoms, a halo-substituted alkyl group containing from 1 to 8 carbon atoms, an alkoxy group containing from 1 to 8 carbon atoms, preferably from 1 to about 4 carbon atoms, an aryl group containing from 6 to 12 carbon atoms, preferably from 6 to about 8 carbon atoms, and an alkylaryl group containing from 7 to 16 carbon atoms, preferably from 7 to about 12 carbon atoms, or $R^4$ and $R^5$ are bonded to each other to form a cycloalkyl group containing from 4 to about 8 carbon atoms, preferably 6 carbon atoms; and wherein formula (I-B) is:

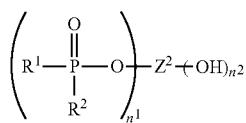

wherein:

$R^1$ and $R^2$, are independently selected from a linear or branched alkyl group containing from 1 to 4 carbon atoms, such as from methyl, ethyl, propyl, isopropyl, butyl, and isobutyl, preferably methyl or ethyl, more preferably both $R^1$ and $R^2$ both being ethyl; and, $n^1$ is an integer equal to or greater than 1, and $n^2$ is one, preferably $n^1$ is from about 1 to about 5 and $Z^2$ is a moiety derived from a diol or polyol which has a valence of $n^1+n^2$, and is of the general formula:

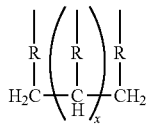

wherein R is selected from the group consisting of:

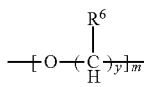

or

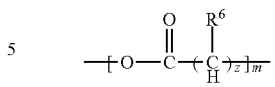

and where each $R^6$ independently is H or is an alkyl of from 1 to 4 carbon atoms, x is 0 or ≥1, preferably 1 to 4, more preferably x=1, y is 2 or 3; z is an integer of from 2 to 5; and, m≥1, preferably m=1.

There is also provided herein a process for the preparation of these compounds.

The novel compounds of formula (I-A) can be prepared by the reaction of mono-hydroxyl-functional-dialkyl phosphinic acids of formula (II) with compounds having an oxirane group, wherein formula (II) is:

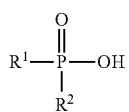

wherein $R^1$ and $R^2$ are as defined.

The compounds of formula (I-A) can also be prepared by the reaction of dialkyl phosphinic halides of formula (III) with aliphatic diols, wherein formula (III) is:

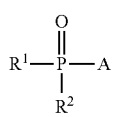

and wherein $R^1$ and $R^2$, are as defined, and A is chlorine or bromine.

The phosphorus-containing diols and/or polyols of the invention, for example those of formula I-B, can be prepared by the reaction of dialkyl phosphinic halides of formula (III) with aliphatic diols and/or polyols.

The reactive mono-hydroxyl-functional dialkyl phosphinates of this invention possess high phosphorus content, have good hydrolytic and thermal stability, exhibit good compatibility with the diol and/or polyol components of the flexible polyurethane foam-forming system, and are useful as highly efficient reactive flame retardants in flexible polyurethane foams.

The present invention further provides fire-retarded flexible polyurethane comprising the reactive residue of said phosphorus-containing mono-hydroxyl-functional compounds after being reacted in the flexible polyurethane foam-forming system to form the flexible polyurethane foam. The phosphorus-containing mono-hydroxyl-functional compounds herein can be used in the flexible polyurethane foam-forming system either individually or in an admixture with one another, and/or with other flame retardants, including halogen-containing flame retardants and phosphorus-containing flame retardants.

All the above and other characteristics and advantages of the invention will be better understood through the following illustrative and non-limitative detailed description of the preferred embodiments thereof.

DETAILED DESCRIPTION OF PREFERRED EMBODIMENTS

In one embodiment the mono-hydroxyl-functional dialkyl phosphinates of formula (I-A) can be those of the more specific formulae (I-A-1) or (I-A-2), wherein formula (I-A-1) is:

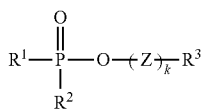
(I-A-1)

wherein $R^1$ and $R^2$, Z, k, and $R^3$ are as defined above; and, wherein formula (I-A-2) is:

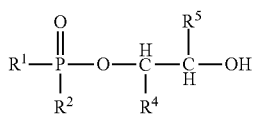
(I-A-2)

and wherein $R^1$, $R^2$, $R^4$ and $R^5$ are as defined above.

In one embodiment herein, the mono-hydroxyl-functional dialkyl phosphinates of formula (I-A) of the present invention are prepared by the reaction of dialkyl phosphinic acids of formula (II) with compounds of formula (IV), having oxirane groups, which formula (IV) is

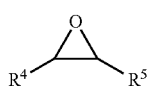
Formula (IV)

wherein:
$R^4$ and $R^5$ are as defined above.

In one other embodiment herein, the mono-hydroxyl-functional dialkyl phosphinates of formula (I-A) of the present invention are prepared by the reaction of dialkyl phosphinic halides of formula (III) with aliphatic diols of formula (V):

HO—(Z)$_K$—R$^3$ (V)

wherein Z, $R^3$ and the subscript k are as defined above.

The phosphorus-containing diols and/or polyols of the present invention, for example those of formula (I-B), are prepared by the reaction of dialkyl phosphinic halides of formula (III) with aliphatic diols or polyols.

The dialkyl phosphinic acids (II) and dialkyl phosphinic halides (III) employed as starting materials in the process of the present invention are for the most part well known in the art. The compounds of formula (II) can be obtained for example by hydrolysis of the corresponding dialkyl phosphinic halides (III). The latter can be prepared for example by the method described in U.S. Pat. No. 3,104,259, the entire contents of which are incorporated by reference herein.

Specific oxirane compounds used in the process for preparing the compounds of formula (I-A) or more specifically (I-A-1) or (I-A-2) of the present invention are selected from the group consisting of, but not limited to, for example, ethylene oxide, propylene oxide, 1,2-epoxybutane, 1,2-epoxypentane, 1,2-epoxyhexane, 1,2-epoxy-5-hexene, 1,2-epoxy-2-methylpropane, 1,2-epoxyoctane, glycidyl methyl ether, glycidyl isopropyl ether, glycidyl isobutyl ether, glycidyl heptyl ether, glycidyl 2-ethylhexyl ether, glycidyl allyl ether, trimethylolpropane triglycidyl ether, styrene oxide, cyclohexene oxide, epichlorohydrin and combinations thereof. More preferably, ethylene oxide, propylene oxide and 1,2-epoxybutane are used as the oxirane compound.

Specific aliphatic diols used in the process for preparing the compounds of formula (I-A) or more specifically (I-A-1) or (I-A-2) of the present invention are selected from the group consisting of, but not limited to, for example, ethylene glycol, diethylene glycol, triethylene glycol, propylene glycol, dipropylene glycol, tripropylene glycol, 1,3-propane diol, 1,4-butane diol, 2-butene-1,4-diol, 1,5-pentane diol, 1,6-hexane diol, 1,8-octane diol, and other diols having molecular weights up to 700.

The aliphatic diols and/or polyols used in the process for preparing the phosphorus-containing polyols of the invention can generally be any suitable diols and/or polyols having at least two or at least three reactive hydrogen atoms, respectively, examples being those having functionality of from 2 or 3 to 6, preferably, 2, 3 and 4, and preferably a molecular weight of from about 100 to about 700. Specific aliphatic diols and/or polyols can be selected from the group of non-polymeric polyalcohols, for example, trimethylol propane, trimethylol ethane or glycerol.

Preferably, the diols and/or polyols to be used according to the present invention are polyether diols and/or polyols. This class of diols and/or polyols is obtained by the ring-opening addition reaction of one or more alkylene oxides (e.g., ethylene oxide and propylene oxide) with a suitable reactant containing one or more active hydrogen atoms, such as alcohols, amine and acids; more specifically, said reactant may be selected from a group consisting of diols, triols, novolac resins, pentaerythritol, sorbitol, sucrose, diethylenetriamine and the like. Polyester-polyols may also be used according to the present invention; this class of polyols is obtained by the condensation reaction of carboxylic, dicarboxylic (or polycarboxylic) acid, such as adipic acid, phthalic acid or the like, with diols or triols. The aliphatic diols and/or polyols used in the process for preparing the phosphorus-containing mono-ols, diols or polyols of the present invention are selected from polymeric diols and/or polyols such as polyether polyols, polyester polyols, and mixtures thereof.

In a preferred embodiment of the present invention, the reaction of dialkyl phosphinic acids (II) with an oxirane compound is carried out in a medium of excess oxirane, with or without an organic solvent such as tetrahydrofuran, 1,4-dioxane, or toluene.

The amount of oxirane compound used in the reaction with mono-hydroxy dialkyl phosphinic acids (II) is a 5-300% molar excess relative to the mono-hydroxy dialkyl phosphinic acid, and preferably a 50-100% molar excess. Using a molar excess of the oxirane compound greater than 100% relative to the mono-hydroxy dialkyl phosphinic acid is inexpedient due to the need to recycle a large quantity of oxirane.

The mono-hydroxyl-functional dialkyl phosphinates of formula (I-A) or more specifically (I-A-1) or (I-A-2) of the present invention have a phosphorus content of about 8-18% by weight and a hydroxyl number of about 150-315 mg KOH/g, depending on the dialkyl phosphinic acid and the oxirane taken for the reaction.

It is preferred, for the preparation of the target mono-hydroxyl-functional dialkyl phosphinates (I-A) or more specifically (I-A-1) or (I-A-2) with the highest possible phosphorus content, to react mono-hydroxy-dialkyl phosphinic acids having the highest phosphorus content amongst the mono-hydroxy dialkyl phosphinic acids (II), with ethylene oxide and propylene oxide.

Thus, the compounds of formula (I-A) or more specifically (I-A-1) or (I-A-2), having particularly valuable properties are those wherein $R^1$, and $R^2$ are each ethyl.

Said reactions are carried out at a temperature of between 40° C. and 120° C., and preferably between 70° C. and 90° C. At a temperature lower than 40° C. the reaction becomes unacceptably slow. On the other hand, applying a temperature higher than 120° C. is not advisable since at such temperatures undesirable decomposition products may be formed.

In a preferred embodiment, the reaction of dialkyl phosphinic halides (III) with an aliphatic diol is carried out in a medium of excess diol.

The amount of diol compound used in the reaction with dialkyl phosphinic halides (III) is generally 2 to 10 moles per 1 mole dialkyl phosphinic halide, and preferably a 4 to 8 moles molar excess. The relatively large excessive amounts of these diols are required for minimizing the formation of undesirable bis(dialkyl phosphinate) esters of glycols and diols having no hydroxyl groups. Using a molar excess of the diol compound greater than 10 moles per 1 mole dialkyl phosphinic halide is inexpedient due to the need to recycle a large quantity of diol.

The mono-hydroxyl-functional dialkyl phosphinates of formula (I-A) or more specifically (I-A-1) or (I-A-2) of the present invention have a phosphorus content of about 2-18% by weight and a hydroxyl number of about 150-450 mg KOH/g, depending on the dialkyl phosphinic halide and the diol taken for the reaction.

It is preferred, for the preparation of the target mono-hydroxyl-functional dialkyl phosphinates (I-A) or more specifically (I-A-1) or (I-A-2) with the highest possible phosphorus content, to react dialkyl phosphinic halides having the highest phosphorus content amongst the dialkyl phosphinic halides (III), with ethylene glycol.

Thus, the compound of formula (I-A-1) having particularly valuable properties, is that wherein $R^1$ and $R^2$ are each ethyl, k is 1, n is 1, Y is —$CH_2CH_2$—, and $R^3$ is hydrogen.

Said reactions are carried out at a temperature of between 25° C. and 120° C., and preferably between 50° C. and 90° C. Applying a temperature lower than 25° C. results in a low yield. On the other hand, applying a temperature higher than 120° C. is not advisable since at such temperatures undesirable decomposition products may be formed. In addition, a catalyst can be used to accelerate reaction for example $MgCl_2$ or $ZnCl_2$.

In a preferred embodiment the reaction of dialkyl phosphinic halides (III) with an aliphatic diol is carried out in the presence of a strong base such as sodium hydroxide or potassium hydroxide, in a medium of both an organic solvent and an excess aliphatic alcohol. The organic solvent is selected from aromatic compounds. Especially suitable aromatic solvents are chlorobenzene, ortho-dichlorobenzene, mesitylene, and in particular, toluene and xylene. An effective amount of the base employed in the process is in a range of 1-1.2 mol per 1 mol dialkyl phosphinic halides (III), and preferably 1-1.05 mol.

Sodium or potassium hydroxide can be employed in a solid form. Water resulting from the reaction between the diol and the base should be eliminated from the reaction mixture as much as possible prior to the addition of dialkyl phosphinic halides (III).

In a preferred embodiment, the reaction of dialkyl phosphinic halides (III) with an aliphatic diol and/or polyol is carried out by varying the degree of partial phosphorylation of the diol and/or polyol. The phosphorus-containing diol and/or polyol according to the present invention comprises at least one phosphorus-containing group. This phosphorus-containing group is a group of formula (III-A).

(III-A)

wherein:
wherein $R^1$ and $R^2$ are as defined, and wherein the wavy line indicates a bond to a diol or polyol via an oxygen atom.

The phosphorus-containing diol and/or polyol of the invention can also comprise two or more phosphorus-containing groups of formula (III-A), wherein these phosphorus-containing groups can be identical or different.

The reaction of dialkyl phosphinic halides (III) with an aliphatic diol and/or polyol can be carried out in the presence of an organic base which is selected from, but not limited to, the group of tertiary amines, for example, triethylamine, pyridine, diisopropyl ethyl amine, 1-methylimidazole. The amount of base used is equimolar to dialkyl phosphinic halide (III). The base can also be used in excess to the dialkyl phosphinic halide. Said reactions are typically carried out in a medium of inert organic solvent. Suitable solvents for the phosphorylation are, but not limited to, halogenated hydrocarbons, such as methylene chloride, chloroform or 1,2-dichloroethane. Solvents which are further suitable are ethers such as dioxane or tetrahydrofuran. Solvents which are further suitable are hydrocarbons such as hexane or toluene.

In a preferred embodiment the reaction of dialkyl phosphinic halides (III) with an aliphatic diol and/or polyol is carried out in the presence of a strong inorganic base such as sodium hydroxide or potassium hydroxide, in a medium of an organic solvent such as chlorobenzene, mesitylene, and in particular, toluene and xylene.

An effective amount of the base employed in the process is in a range of 1-1.2 mol per 1 mol dialkyl phosphinic halides (III), and preferably 1-1.05 mol. Sodium or potassium hydroxide can be employed in a solid form. Water resulting from the reaction between the diol, and/or polyol and the base should be eliminated from the reaction mixture as much as possible prior to the addition of dialkyl phosphinic halides (III).

The amounts of dialkyl phosphinic halide (III) and diol and/or polyol can be adjusted so that the desired degree of functionalization is attained. Partial phosphorylation of the diol and/or polyol can be achieved by using less than the stoichiometric amount of the dialkyl phosphinic halide (III) to the diol and/or polyol based on its functionality. In this way, only a portion of the OH groups in the diol and/or polyol is reacted with dialkyl phosphinic halide.

The phosphorus-containing diol and/or polyol of the present invention (also described herein as the partially phosphorylated diol and/or polyol) has a remaining average OH— functionality (following phosphorylation thereof) of 1 and a molecular weight of from about 200 to about 1000. The phosphorus-containing diols and/or polyols of the present invention have a phosphorus content of about 4-20% by weight and a hydroxyl number of about 20-800 mg KOH/g, depending on the dialkyl phosphinic halide and the diol and/or polyol taken for the reaction, and on the molar ratio between them.

The diol and/or polyol phosphorylation reactions are carried out at a temperature of between 0° C. and 100° C., and preferably between 10° C. and 90° C. Applying a temperature lower than 0° C. results in a low reaction rate. On the other hand, applying a temperature higher than 100° C. is not advisable since at such temperatures undesirable decomposition products may be formed.

The following examples illustrate specific embodiments of both the preparation of certain compounds of the invention and the utility of these compounds as reactive flame retardants in flexible polyurethane foams.

The compounds of the invention are useful as reactive flame retardants. The flame retardants may be used as-is, or as a mixture with halogenated or non-halogenated products. For flexible polyurethane foams it is preferred to use halogen-free hydroxyl-functional dialkyl phosphinates of the invention either pure or with other non-halogenated products.

The compounds of the present invention are highly efficient reactive flame retardants when incorporated into flexible polyurethane foams. It should be noted that the compounds of the invention are useful over a broad Isocyanate Index (abbreviated herein MDI or TDI). The index refers to the ratio of isocyanate practically used in the formulation vs. the theoretical stoichiometric amount of isocyanate required, expressed in percentages.

The flexible polyurethane foams herein contain a typical flame-retardant-effective amount of the composition of this invention. Typically, the compositions of this invention are applied in amounts that provide a total phosphorus concentration in the polymer (i.e., the flexible polyurethane foam) in the range of 0.3 to 15 wt %, based on the total weight of the polymer. Preferably, the total phosphorus concentration in the polymer is in the range of 1 to 10 wt % and more preferably, in the range of 1.5 to 5 wt %, based on the total weight of the flexible polyurethane polymer. Most preferably, the amounts used of the reactive flame retardants of this invention are at least sufficient to meet the current requirements of the flammability Test Method MVSS 302.

By suitable choice of components and conditions, the flexible polyurethane foams are made which may vary in properties as to the degree of flexibility. Thus, flexible foams are generally made from polymeric diols or triols having hydroxyl numbers of from 20 to 80 using water as the principal foaming agent.

The flexible polyurethane foams of the present invention can contain the appropriate choice of auxiliary agents, for example catalysts, surfactants, foam stabilizers and the like.

Flexible polyurethane foams as used herein is made using a diol and/or polyol having a 3,000 to about 6,000 molecular weight diol and/or polyol as described herein, e.g., a polyether triol prepared by the addition of propylene oxide to glycerol. A flexible polyurethane foam as used herein is characterized by having a core impact resilience of at most 30% and a glass transition point of from −80° C. to −60° C. Here, the flexible polyurethane foam preferably has a hard segment content of at most 40 mass %. Conventional flexible polyurethane foam having a bulk foam density of 2.5 pounds per cubic foot (PCF) or lower and having a foam hardness or IFD (measured in accordance with test method ASTM 3574-Test B1) in a range of 10 to 90 lb/50 in$^2$.

The method of making the flexible polyurethane foam of the invention can comprise combining the diol and/or polyol component and/or the isocyanate component or catalyst and one or more of the flame retardant materials of Formulae (I-A), (I-A-1), (I-A-2) and (I-B) described herein which may be metered and pumped into a common mixing vessel, and then the resulting mixture may easily be moved to the polymerization site for use in molds, slab stock operations, etc.

The reactive flame retardants of the invention herein may also be admixed with the diol and/or polyol reactant before combination with the isocyanate reactant. It is also within the scope of the invention to mix the reactive flame retardant materials with the isocyanate before combining such mixture with the diol and/or polyol reactant. However, if the isocyanate and the aforementioned flame retardant materials are mixed and allowed to stand at room temperature for a substantial period of time, reaction may occur. The "reaction product" as used in the claims and specification herein, can in one embodiment comprise reacting the contents of the flexible polyurethane foam-forming system in any one of the aforementioned methods, and may further include reacting the reactive flame retardant via a pre-polymer technique, such as for example, reacting an excess of isocyanate with polyol to form an isocyanate terminated pre-polymer and then further reacting the prepolymer with the reactive flame retardant herein.

The flame retardant materials of Formulae (I-A), (I-A-1), (I-A-2) and (I-B) described herein may be described as isocyanate-reactive (NCO-reactive) materials, i.e., they are reactive with the isocyanates through the hydroxyl group(s).

The diols and/or polyols used in making the flexible polyurethane foams described herein can include any organic polyol, including diols, polyols, and polyether, polyester, polyesteramide polyols having hydrogen atoms that are reactive with isocyanates may be used. Generally, these materials have molecular weights ranging from about 62 to about 5,000 and have from 2 to about 10 or more hydroxyl groups per molecule and weight percent hydroxyl contents ranging from about 0.5 to about 25%. The generally have hydroxyl numbers of from about 50 to as high as 500 or even 700.

In the polyester-polyol type of reactant the acid number should be less than 10 is usually as close to 0 as possible. These materials are referred to conveniently as the "polyol" reactant. The useful active hydrogen-containing diol and/or polyols include the large family of adduct compounds which result when ethylene oxide, propylene oxide, 1,2- and 2,3-butylene oxide, or other alkylene oxides are added to such active hydrogen compounds such as diols, glycols and polyols presented by ethylene glycol, propylene glycol, glycerine, methyl glucoside, sucrose, sorbitol, hexanetriol, trimethylol propane, pentaerythritol as well as various alkylamines and alkylenediamines, and polyalkylenepolyamines and the like. Various amounts of these alkylene oxides may be added to the base diol, polyol or amine molecules referred to, depending upon the intended use of the polyurethane.

For example, a diol and/or polyol for use in making flexible foams could be well represented by glycerine to which sufficient propylene oxide was added to give a final hydroxyl content of about 1.7%. Such a material would have a molecular weight of about 3,000 and have a molar ratio of glycerine to propylene oxide of about 1 glycerine to 50 propylene oxide.

This technique of controlling flexibility by selection of the diol and/or polyol molecule and the subsequent amount of alkylene oxide added is well known to those in the art.

In addition to the glycols and the like which can serve as the base polyol molecule for addition of the alkylene oxides and thus yield the "polyol" molecule for reaction with the isocyanate, one can use a starting molecule which contains primary and/or secondary amine groups which have hydrogen reactive toward alkylene oxides. Here also, the quantity of alkylene oxide added depends on the intended uses of the final polyurethane products. In the flexible polyurethane products herein alkylene oxide would be used to produce polyols with lower hydroxyl content, such as from about 0.1% to about 5% or 10%.

Representative amines which may serve as active-hydrogen containing molecules for reaction with epoxides are those having from 1 to about 6 or more amino nitrogens, examples of which are ethyl amine, ethylene diamine, diethylenetriamine, triethylenetetramine, tetrapropylenepentamine and other linear saturated aliphatic alkylene amines, the important requirement being at least two, and preferably more, say 3 to 8 or 10 active hydrogen sites to which the alkylene oxide may be added.

It is also well known to use the hydroxyl bearing molecules which have been prepared by esterification type reactions from polyfunctional acids or anhydrides and polyfunctional alcohols as the active hydrogen compounds used in preparing the polyurethane systems. These compounds are often called polyester polyols. Typical acids used in making these polyester polyols are maleic, phthalic, succinic, fumaric, tetrahydrophthalic, chlorendic, and tetrachlorophthalic acids. Typical diols and/or polyols are ethylene, propylene, butylene, diethylene, and dipropylene, glycols, and polyethylene, polypropylene, glycols and glycerine, trimethylol propane, hexanetriol, pentaerythritol, sorbitol and the like. Where available the above mentioned acids may be used in the anhydride form if desired.

In making the polyester-polyols, any of the various polyfunctional acids or anhydrides or mixtures thereof are caused to react with any of the diols, glycols or polyols or mixtures thereof, using a stoichiometric excess of the hydroxyl groups such that the final polyol product contains predominantly hydroxyl end groups. The degree of hydroxyl functionality and the percent hydroxyl is easily varied to provide the desired polyols by technology and techniques which are known to those skilled in the art.

In the art and technology of making flexible polyurethanes, it is also known to employ what is called prepolymer techniques. This is a technique wherein part of the reaction involved in making flexible polyurethane is carried out yielding a prepolymer of increased molecular weight and with either resultant end groups of hydroxyls or isocyanates depending on the stoichiometric used in making this prepolymer. This prepolymer is then used to prepare the final flexible polyurethane product by reacting it with either a isocyanate or polyol, depending on, as mentioned above, whether the terminal groups of the prepolymer are hydroxyls or isocyanates, respectively.

Broadly, any of the prior art polyesters, isocyanate-modified-polyester prepolymers, polyesteramides, isocyanate-modified-polyesteramides, alkylene glycols, isocyanate-modified alkylene glycols, polyoxyalkylene glycols, isocyanate-modified polyoxyalkylene glycols, etc., having free reactive hydrogens and especially hydroxyl groups may be employed for the production of the polyurethanes described herein.

Examples of isocyanates which can be used include those having two or more isocyanate groups which have heretofore been used for making flexible polyurethane foams. Examples of such isocyanate compounds include aromatic isocyanates, aliphatic isocyanates and alicyclic isocyanates, as well as mixtures of two or more of such isocyanates, and modified isocyanates obtained by the modification of such isocyanates. Specific examples of such isocyanates are toluene diisocyanate, diphenylmethane diisocyanate, polymethylene polyphenylene polyisocyanate (crude MDI), xylylene diisocyanate, isophorone diisocyanate and hexamethylene diisocyanate; and modified products of such isocyanates, such as carbodiimide-modified products, biuret-modified products, dimers and trimers. Prepolymers with terminal isocyanate groups obtained from such isocyanates and active hydrogen-containing compounds can also be used.

In one embodiment, the isocyanate index range for flexible polyurethane foams can be from about 130 to about 80, more preferably, from about 120 to about 90 and most preferably from about 115 to about 95.

As the blowing agent in the flexible polyurethane foam-forming composition of the present invention, known blowing agents heretofore used in such compositions are suitably selected according to the properties required of the foamed product.

In the present invention, a cross-linking agent is also used as the case requires.

As the cross-linking agent, a compound having at least two functional groups having active hydrogen, such as hydroxyl groups, primary amino groups or secondary amino groups is preferred. However, in a case where a polyol compound is used as the cross-linking agent, the following is taken into account. Namely, a polyol compound having a hydroxyl value of at least 50 mg KOH/g and more than four functional groups, is considered to be the cross-linking agent, and a polyol which does not satisfy this, is considered to be any one of polyols of the above-mentioned polyol mixture (polyol (1), (2) or other polyol). Further, two or more cross-linking agents may be used together. As specific examples, a polyhydric alcohol such as dextrose, sorbitol or sucrose; a polyol having an alkylene oxide added to a polyhydric alcohol; an amine compound such as monoethanolamine, diethanolamine, ethylenediamine, 3,5-diethyl-2,4 (or 2,6)-diaminotoluene (DETDA), 2-chloro-p-phenylenediamine (CPA), 3,5-bis(methylthio)-2,4 (or 2,6)-diaminotoluene, 1-trifluoromethyl-4-chloro-3,5-diaminobenzene, 2,4-toluenediamine, 2,6-toluenediamine, bis(3,5-dimethyl-4-aminophenyl)methane, 4,4'-diaminodiphenylmethane, m-xylylenediamine, 1,4-diaminohexane, 1,3-bis(aminomethyl)cyclohexane or isophoronediamine; and a compound obtained by adding an alkylene oxide thereto, may, for example, be mentioned.

When the above cross-linking agent is used, even in a case where, for example, a large amount of a blowing agent is used to produce a flexible foam having a low density, the foaming stability will be good, and it will be possible to produce such a flexible foam. Especially when a diol and/or polyol having a high-molecular weight is used, it is possible to produce a flexible foam having a low density which used to be considered difficult to foam. Further, when the cross-linking agent is used, the durability will be improved, as compared with a case where it is not used. In a case where a diol and/or polyol having a high-molecular weight is used as in the present invention, the foaming stability can readily be improved particularly when a compound having a relatively high-molecular weight, such as a molecular weight of at least 4000, is used.

Water is a typical example of such a blowing agent; other examples include methylene chloride, n-butane, isobutane, n-pentane, iso-pentane, dimethyl ether, acetone, carbon dioxide, and the like. Depending on the desired density and other properties of the foamed polyurethane, these and other blowing agents can be used alone or in combinations of two or more in a manner known in the art.

The amount of blowing agent to be used is not particularly limited but will ordinarily range from 0.1 to 20 parts by weight per 100 parts by weight of the diol and/or polyol component of the foam-forming composition. Preferably, the amount of blowing agent(s) will be such as to provide a foam density of from 0.8 to 2.5 pounds per cubic foot, and preferably from 0.9 to 2.0 pounds per cubic foot.

The polyurethane foam-forming composition herein can preferably contain any of the catalysts, and combination of catalysts, heretofore known or used for the production of polyurethane foams. Examples of useful catalysts include sodium hydroxide, sodium acetate, tertiary amines or materials which generate tertiary amines such as trimethylamine, triethylene diamine, N-methyl morpholine, N,N-dimethyl cyclohexylamine, and N,N-dimethyl aminoethanol. Also applicable are metal compounds such as hydrocarbon tin alkyl carboxylates, dibutyl tin diacetate, dibutyl tin dioctoate dibutyl tin dilaurate and stannous octoate; as well as other compounds intended to promote trimerization of the isocyanate such as, 2,4,6-tris(N,N-dimethylamino-methyl)phenol, 1,3,5-tris(N,N-dimethyl-3-aminopropyl)-S-hexahydrotriazine, potassium octoate, potassium acetate and catalysts such as DABCO TMR® and POLYCAT 43®.

Many other kinds of catalysts can be substituted for those listed above, if desired. The amount of catalyst used can advantageously range from 0.05 to 5 weight percent or more based on the total weight of diol and/or polyol in the foam-forming mixture.

The isocyanate (NCO) index which is applied in making the flexible foam according to the present invention is 95-125 and preferably 100-120. It is commonly understood that the NCO index of polyurethane foams is from about 80-130.

The densities of the flexible polyurethane foams herein may range of from 14-80 and preferably 16-55 and most preferably 20-40 kg/m$^3$.

Surfactants, including organic surfactants and silicone-based surfactants, may be added to serve as cell stabilizers. Some representative materials are sold under the designations SF-1109, L-520, L-521 and DC-193, which are, generally, polysiloxane polyoxylalkylene block copolymers. Also included are organic surfactants containing polyoxy-ethylene-polyoxybutylene block copolymers. It is particularly desirable to employ a minor amount of a surfactant to stabilize the foaming reaction mixture until it cures. Other surfactants that may be useful herein are polyethylene glycol ethers of long-chain alcohols, tertiary amine or alkanolamine salts of long-chain allyl acid sulfate esters, alkylsulfonic esters, alkyl arylsulfonic acids, and combinations thereof. Such surfactants are employed in amounts sufficient to stabilize the foaming reaction against collapse and the formation of large uneven cells. Typically, a surfactant total amount from about 0.2 to about 3 wt %, based on the formulation as a whole, is sufficient for this purpose. However, it may be in some embodiments desirable to include some surfactants, e.g., DABCO DC-5598, available from Air Products and Chemicals, Inc., in a higher amount. In view of this a surfactant may be included in the inventive formulations in any amount ranging from 0 to 6 wt. %, based on the diol and/or polyol component.

Finally, other additives such as fillers and pigments may be included in the polyurethane foam-forming formulations described herein. Such may include, in non-limiting embodiments, barium sulfate, calcium carbonate, graphite, carbon black, titanium dioxide, iron oxide, microspheres, alumina trihydrate, wollastonite, prepared glass fibers (dropped or continuous), polyester fibers, other polymeric fibers, combinations thereof, and the like. Those skilled in the art will be aware without further instruction as to typical and suitable means and methods to adapt the inventive formulations to produce flexible polyurethane foams that, though still falling within the scope of the claims appended hereto, exhibit or benefit from desired property and/or processing modifications.

The flexible polyurethane foams described herein, be they be can be utilized in the construction and formation of various articles such as furniture, bedding, and automotive seat cushions, more specifically, furniture applications, automotive applications, boating applications, bus seating applications, train seating applications, RV seating applications, office furniture seating applications, aviation applications, tractor applications, bicycle applications, engine mount applications, compressor applications, bedding applications, insulation applications, sporting goods applications, shoe applications, carpet cushioning applications, packaging applications, textile applications, buffer cushioning applications, HVAC applications, tent applications, life raft applications, luggage applications, and hand bag applications.

Flexible slabstock polyurethane foam can be used for furniture, e.g., upholstered furniture, such as cushions, backs and arms, the automotive industry, such as seat and back cushions, and head linings and head rests, for automobiles and trucks, for public transport seating, such as busses and airplanes, as well as in any of tractor, bicycle and motorcycle seats including, but not limited to vehicle seat bottom and back bolsters, and armrests, as well as support rings for run flat tires, and other automobile interior components; bedding such as mattresses, as sound insulation materials, automobile interior components such as an arm rest, a steering wheel and a shift lever knob, shoe soles, and sporting goods.

EXAMPLES

Preparation Example 1

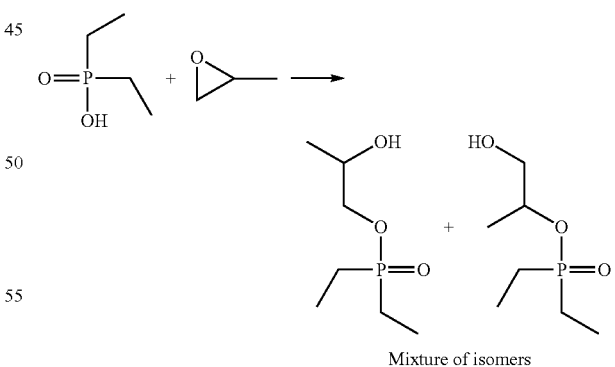

Mixture of isomers

A 2-liter, jacketed, hastelloy reactor equipped with a mechanical stirrer, oil heater and positive displacement laboratory pump was charged with diethyl phosphinic acid (779 g, 6.38 mol) and sealed. The reactor was heated to an internal temperature of 45° C. Propylene oxide (743 g, 12.77 mol) was added to the reactor via the pump over two hours with the temperature being maintained below 65° C. Subsequently the reactor internal temperature was increased to 90° C. and maintained there for three hours. The excess propylene oxide was evaporated and the residue was distilled under vacuum (300-500 mTorr) using a wiped film evaporator at a jacket temperature of 125° C. The target fraction was collected as a clear, colorless liquid. The yield was 90% with respect to the starting diethyl phosphinic acid. The product was a mixture of two isomers of hydroxyl-functional esters of diethyl phosphinic acid, $^{31}P$ NMR (acetic acid-$d_4$, ppm): 66.8-67.7; and had an acid# of 0.4 mg KOH/g and a phosphorus content of 15.9%.

Preparation Example 2

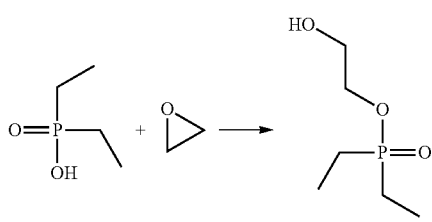

A 1-liter flask, with a heating mantle, mechanical stirrer, reflux condenser, dip tube, j-chem controller and thermocouple, and caustic scrubber was charged with diethyl phosphinic acid (469 g, 3.84 mol). The flask was heated to 80° C. and ethylene oxide from a pressurized cylinder was charged into the reactor through the dip tube over five hours. Final molar ratio of ethylene oxide to diethyl phosphinic acid was 1.33. The reaction mixture was kept at 80° C. for additional three hours. Further nitrogen was passed through the dip tube to remove the excess ethylene oxide. A batch distillation of the residue was done at 150° C. and 200 mTorr resulting in a clear liquid (400 g). The product was 2-hydroxyethyl ester of diethyl phosphinic acid, $^{31}P$ NMR ($CDCl_3$, ppm): 79; and had an acid# of 0.4 mg KOH/g.

Application of the new compounds of the present invention is demonstrated through their use as flame retardants in standard formulations for flexible polyurethane foams (Application Example 3).

In addition to the new flame retardant compounds, the following components were used in preparation of the polyurethane foams:

| Materials | Manufacturer |
|---|---|
| Voranol 8136 Polyether Polyol | Dow |
| Desmophen 60WB01 Polyester Polyol | Covestro |
| Niax A-1 amine catalyst | Momentive |
| Niax C-131 NPF | Momentive |
| Niax DMP | Momentive |
| Niax L-537XF | Momentive |
| Niax L-620 | Momentive |
| Dabco 33 LV amine catalyst | Air Products |
| T-9 Stannous octoate catalyst | Air products |
| TDI 80 | Everchem Specialty Chemicals |
| TDI 65 | Everchem Specialty Chemicals |
| New FR Product (from Example 1) | ICL |
| Fyrol PR-2, Fyrol A300-TB | ICL |

Application Example 3

Foam samples were prepared by mixing the polyol and the New FR Product from Preparation Example 1. The remaining components of the formulation, including water, amine catalyst, silicone surfactant and tin catalyst (except for the isocyanate), were added and stirred into the polyol/FR Product mixture at 2000 rpm for 30 seconds for polyether foam, and 1000 rpm for 60 seconds for polyester foam. Immediately after addition and incorporation of the isocyanate into the reaction mixture with vigorous stirring, the complete reaction mixture was then poured into an 8×8×5" (20×20×20 cm) box and allowed to rise fully. For polyether foam, the box was then placed in a ventilated hood for 24 hours curing at room temperature; for polyester foam, the box was first placed and cured at 110° C. oven for 10 minutes, followed by 24 hours curing at room temperature. The top and bottom 0.5" of the foam sample was removed, as well as the paper lining sides of the foam. Samples were then cut and tested for flammability, including Federal Motor Vehicle Safety Standard No. 302 (FMVSS 302), emission test per VDA 277.

Table 1 and 2 present the ingredients, parameters for the foam preparation and the results of the tests.

TABLE 1

Polyether flexible foam formulation system and test results

| Formulation (parts by weight) | Foam 1 | Foam 2 | Foam 3 |
|---|---|---|---|
| Polyol Voranol 8136 | 100 | 100 | 100 |
| Flame Retardant | — | Fyrol FR-2 | New FR Product |
| FR Loading | — | 8.00 | 4.00 |
| Water | 3.55 | 3.55 | 3.55 |
| Niax A-1 | 0.06 | 0.06 | 0.06 |
| Dabco 33LV | 0.19 | 0.19 | 0.19 |
| Niax L-620 | 0.80 | 0.80 | 0.80 |
| Stannous Octoate T-9 | 0.10 | 0.10 | 0.05 |
| TDI Index | <110> | <110> | <110> |
| Physical Properties | | | |
| Density (pcf) | 1.80 | 1.96 | 1.95 |
| Air Flow (scfm) | 3.0 | 3.0 | 2.8 |
| Flame/Emission Tests | | | |
| FMVSS 302 (13 mm thickness) | Fail | SE | SE |
| VDA 277 Total Carbon Emission (μgC/g) | 5.64 | 5.76 | 2.56 |

SE = Self-Extinguishing-Specimen, ignited but self-extinguished prior to entering the time zone

TABLE 2

Polyester flexible foam formulation system and test results

| Formulation (parts by weight) | Foam 4 | Foam 5 | Foam 6 |
|---|---|---|---|
| Desmophen 60WB01 | 100 | 100 | 100 |
| Flame Retardant | — | Fyrol A300-TB | New FR Product |
| FR Loading | — | 7 | 4 |
| Water | 4.0 | 4.0 | 4.0 |
| Niax C-131NPF | 1.1 | 1.1 | 1.1 |
| Niax DMP | 0.2 | 0.2 | 0.2 |
| Niax L-537XF | 1.3 | 1.3 | 1.3 |
| TDI Index (40% TDI80/60% TDI65) | <98> | <98> | <98> |
| Physical Properties | | | |
| Density (pcf) | 1.87 | 1.99 | 1.92 |
| Air Flow (scfm) | 0.5 | 0.6 | 0.4 |

TABLE 2-continued

Polyester flexible foam formulation system and test results

| Formulation (parts by weight) | Foam 4 | Foam 5 | Foam 6 |
|---|---|---|---|
| Flame/Emission Test | | | |
| FMVSS 302 (13 mm thickness) | Fail | SE | SE |
| VDA 277 Total Carbon Emission (μgC/g) | 4.23 | 5.50 | 3.21 |

While the invention has been described with reference to certain embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed as the best mode contemplated for carrying out this invention but that the invention will include all embodiments falling within the scope of the appended claims.

The invention claimed is:

1. A flame-retarded flexible polyurethane foam comprising the reaction product of a polyol, an isocyanate and a flame retardant-effective amount of a mono-hydroxyl-functional dialkyl phosphinate compound of the formula (I-A):

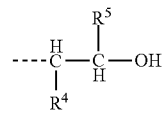

(I-A)

wherein:

$R^1$ and $R^2$ are selected from a linear or branched alkyl group containing from 1 to 4 carbon atoms; and, X is either ------$(Z)_k$—$R^3$ or

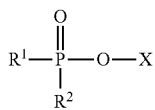

and when X is ------$(Z)_k$—$R^3$, Z is —$(Y-O)_n$—, wherein Y is a linear or branched alkylene group containing from 2 to 8 carbon atoms and n represents an integer from 1 to 20;

k may be 0 or 1;

$R^3$ is selected from hydrogen, a mono-hydroxy-terminated linear or branched alkylene group containing from 2 to about 8 carbon atoms; and, provided that when k is zero, $R^3$ is the mono-hydroxy-terminated linear or branched alkylene group and when k is 1, $R^3$ is hydrogen, and when X is

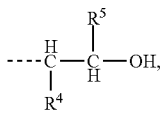

$R^4$ and $R^5$ are each independently selected from H, a linear or branched alkyl group containing from 1 to 8 carbon atoms, a linear or branched alkenyl group containing from 2 to 8 carbon atoms, a halo-substituted alkyl group containing from 1 to 8 carbon atoms, an alkoxy group containing from 1 to 8 carbon atoms, an aryl group containing from 6 to 12 carbon atoms and an alkylaryl group containing from 7 to 16 carbon atoms, or $R^4$ and $R^5$ are bonded to each other to form a cycloalkyl group containing from 5 to about 8 carbon atoms.

2. The flame-retarded flexible polyurethane foam of claim 1, wherein $R^1$ and $R^2$ are each an ethyl group.

3. The flame-retarded flexible polyurethane foam of claim 1, wherein the mono-hydroxyl-functional dialkyl phosphinate compound has the formula (I-A-1):

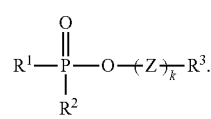

(I-A-1)

4. The flame-retarded flexible polyurethane foam of claim 3, wherein $R^1$ and $R^2$ are each an ethyl group.

5. The flame-retarded flexible polyurethane foam of claim 1 wherein the mono-hydroxyl-functional dialkyl phosphinate compound has the formula (I-A-2):

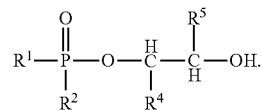

(I-A-2)

6. The flame-retarded flexible polyurethane foam of claim 5, wherein $R^1$ and $R^2$ are each an ethyl group.

7. An article comprising the polyurethane foam of claim 1.

8. The article of claim 7, wherein the article is suitable for use in an application selected from the group consisting of furniture applications, automotive applications, boating applications, bus seating applications, train seating applications, RV seating applications, office furniture seating applications, aviation applications, tractor applications, bicycle applications, engine mount applications, compressor applications, bedding applications, insulation applications, sporting goods applications, shoe applications, carpet cushioning applications, packaging applications, textile applications, buffer cushioning applications, HVAC applications, tent applications, life raft applications, luggage applications, and hand bag applications.

9. The article of claim 8, wherein said furniture applications are selected from upholstered furniture applications.

10. The article of claim 8, wherein said automotive applications are selected from the group consisting of automotive seat cushions, head linings and head rests, back cushions for automobiles and trucks, bus seating, vehicle seat bottom and back bolsters, armrests, and support rings for run flat tires.

11. The article of claim 8, wherein said bedding applications are selected from the group consisting of mattresses and mattress top applications.

12. The article of claim 8, wherein said insulation applications are sound insulation applications.

* * * * *